United States Patent [19]
Wakasugi

[11] Patent Number: 5,336,503
[45] Date of Patent: Aug. 9, 1994

[54] ANTI-PEPTIC ULCER AGENT

[75] Inventor: Junichiro Wakasugi, Tokyo, Japan

[73] Assignee: Daiichi Pharmaceutical Co., Ltd., Tokyo, Japan

[21] Appl. No.: 861,310

[22] Filed: Mar. 31, 1992

[51] Int. Cl.$^5$ ................................. A61K 9/48
[52] U.S. Cl. ........................ 424/451; 424/464; 424/489
[58] Field of Search ............... 424/451, 464, 489; 514/927; 544/107, 361

[56] References Cited

U.S. PATENT DOCUMENTS 4,529,602 7/1985 Wada ........................... 544/107
5,030,631 7/1991 Bauer .......................... 544/361

Primary Examiner—Thurman K. Page
Assistant Examiner—William E. Benston, Jr.
Attorney, Agent, or Firm—Sughrue, Mion, Zinn, Macpeak & Seas

[57] ABSTRACT

A pharmaceutical composition for treating a peptic ulcer, which comprises a myosin light chain kinase inhibitor as an active ingredient and a pharmaceutical additive. The myosin light chain inhibitor reduced the gastric acid secretion and is considered an excellent anti-ulcer agent.

6 Claims, 3 Drawing Sheets

ANTI-PEPTIC ULCER AGENT

FIELD OF THE INVENTION

This invention relates to a composition and method of treating or preventing agent for peptic ulcer which comprises an inhibitor for myosin light chain kinase (hereinafter abbreviated as MLCK) as an active ingredient.

BACKGROUND OF THE INVENTION

The presence of unbuffered acid appears to be an essential contributory factor in the pathogenesis of peptic ulcers such ae gastric ulcer, duodenal ulcer gastritis and the like. Therefore, the treatment of the peptic ulcer has concentrated on the reduction of acidity, that is, an inhibition of gastric acid secretion. In view of this, an $H_2$-antagonist such as cimetidine, famotidine, ranitidine and a proton pump inhibitor such as omeprazole have been developed and used clinically as anti-ulcer agents.

Acid secretion by the stomach is carried out by the parietal cells of the gastric epithelium. Histamine, gastrin and acetylcholine directly bind to their respective receptors in a parietal cell that induces a cascade of intracellular events inducing acid secretion. The initial events involve changes in the concentration of intracellular second messengers. Histamine receptor linked to adenylate cyclase influences intracelluar levels of cAMP which causes an increase in protein kinase A activity and cytoplasmic $Ca^{2+}$ concentration (hereinafter abbreviated as $[Ca^{2+}]i$). The occupation of gastrin and muscarinic receptors leads to 1,4,5-inositol triphosphate (hereinafter abbreviated as 1,4,5-$IP_3$) formation which causes a release of $Ca^{2+}$ from intracellular store.

The secretagogue such as histamine, gastrin, or acetylcholine stimulates gastric acid secretion accompanied by dramatic transformation of the parietal cell cytoskeletal structure, rapid changes in enzyme location and activity, and opening of ion channels.

That is, the resting parietal cell contains a collapsed canalicular system and cytoplasmic tubulovesicles contain the gastric proton pump $H^+,K^+$-ATPase. Stimulation of parietal cells by those secretagogues induces formation of a dense apical meshwork of intracellular canaliculi packed with long microvilli. The apical membrane surface area increases 5- to 10-fold after stimulation. This increase coincides with the disappearance of the majority of cytoplasmic tubulovesicles seen in a resting parietal cell. The mechanism of this increase in membrane surface area appears to arise from a fusion of tubulovesicles and apical membrane including translocation of $H^+,K^+$-ATPase from tubulovesicles in the resting cell to the apical membrane in the stimulated cells. The fusion of tubulovesicles with the apical membrane is directed by cytoskeletal microfilaments composed of actin and other proteins such as myosin. Membrane is recycled back to tubulovesicles as cells return to the resting state, and this process also appears to be mediated by actincontaining microfilaments. The actin mediate $H^+,K^+$-ATPase translocation which is an essential and important process in the initiation of gastric acid secretion in parietal cells (Text Book of Gastroenterolgy, J. B. Lippincott Page 246 1991).

The myosin commonly associated with actin and is found in the parietal cell. MLCK is a $Ca^{2+}$-calmodulin dependent enzyme which mediates the phosphorylation of myosin light chain and is considered to play an important role in the regulation of the contractility of actomyosin system, that is, cytoskeletal microfilaments.

With the above mechanism of the gastric acid secretion, an $H_2$ antagonist blocks the reaction after stimulation due to histamine gastrin or muscarinic receptor activation. Also, a proton pump inhibitor directly inhibits $H^+,K^+$-ATPase activity.

However, no suggestion has been made that MLCK inhibitor may inhibit the transformation of a parietal cell to inhibit gastric acid secretion, and the role of myosin and MLCK in the process of gastric acid secretion has never been examined.

SUMMARY OF THE INVENTION

The inventor of the present invention discovered that MLCK inhibitor can inhibit the secretion of gastric acid, and the inhibition can be specific at the step of the parietal cell transformation due to the secretagogues, and then he completed the present invention.

Thus, the present invention relates to a composition and method of treating or preventing agent for peptic ulcer which comprises a MLCK inhibitor as an active ingredient.

DETAILED DESCRIPTION OF THE INVENTION

Figure 1:
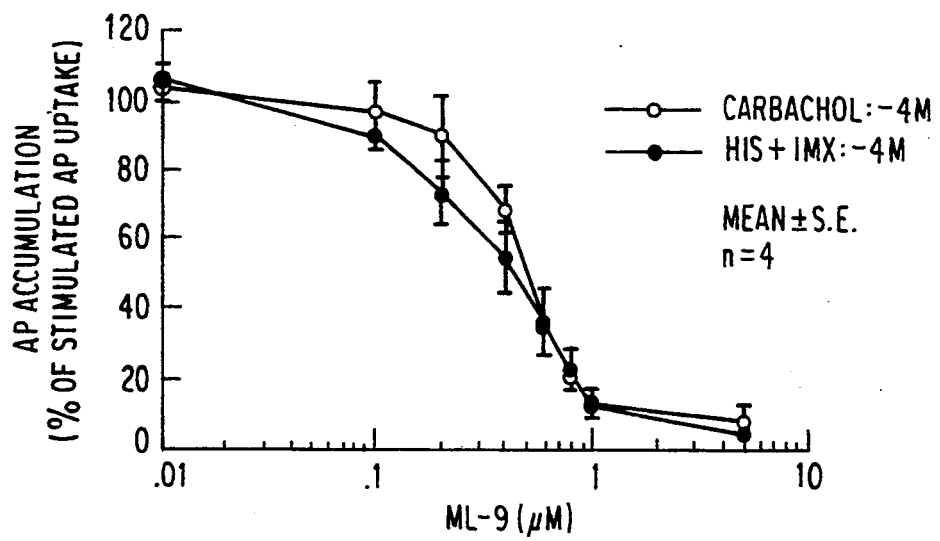
FIG. 1 and FIG. 2 demonstrate the effect of 1-(5-chloronaphthalene-1-sulfonyl)-1H-hexahydro-1,4-diazepine hydrochloride, ML-9 on [$^{14}$C]AP uptake of secretagogue stimulated parietal cells.

Peptic ulcers to which the present invention is applicable include gastric ulcer, duodenal ulcer, gastritis and the like.

The MLCK inhibitor of the present invention designates compounds which can act specifically on MLCK itself and which inhibit the activity of this enzyme. Examples thereof include 1-(5-chloronaphthalene-1-sulfonyl)-1H-hexahydro-1,4-diazepine hydrochloride (herein abbreviated as ML-9), 1-(5-iodonaphthalene-1-sulfonyl)-1H-hexahydro-1,4-diazepine hydrochloride (herein abbreviated as ML-7), KT5926 and the like (J. Biol. Chem., 262 7796–7801 1987).

MLCK requires $Ca^{2+}$-calmodulin to mediate the phosphorylation of the light chain of myosin. Therefore, calmodulin antagonist or a $Ca^{2+}$ blocker may act similarly as an MLCK inhibitor does. However, the administration of these antagonists and blockers for the treatment of peptic ulcer is not preferable because of the greater number of regulatory effects of antagonists or blockers than the regulatory effect of the MLCK inhibitor.

The MLCK inhibitor can be formulated in various pharmaceutical preparations, such as tablets, powders, capsules, granules, injectable solutions and the like, by using known pharmaceutical techniques with appropriate pharmaceutically acceptable additives, such as binders (hydroxypropylcellulose, etc.), ingredients (lactose, corn starch, etc.), disintegrators (carboxy-methylcellulose calcium, etc.) and the like.

Examples of those preparations are as follows.

| Tablets | |
|---|---|
| MLCK Inhibitor | 100 mg |
| Lactose | 75 mg |
| Corn Starch | 16.2 mg |
| Carboxymethylcellulose Calcium | 5 mg |
| Hydroxypropylcellulose | 3.3 mg |
| Magnesium Stearate | 0.5 mg |
| Capsules | |
| MLCK Inhibitor | 100 mg |
| Corn Starch | 18.9 mg |
| Low Substituted Hydroxypropylcelluose | 15 mg |
| Light Unhydrous Silicic Acid | 0.3 mg |
| Magnesium Stearate | 0.8 mg |
| MLCK Inhibitor | 50 mg |
| Corn Starch | 84.4 mg |
| Light Unhydrous Silicic Acid | 0.1 mg |
| Magnesium Stearate | 0.5 mg |

The MLCK inhibitor can be administered orally or parenterally. The dose level of the MLCK inhibitor usually ranges from about 1 to about 1000 mg/day/adult (body weight, about 65 kg) for oral administration and, if necessary, the dose can be changed depending on the degree of the disease.

The MLCK inhibitor used to the present invention inhibited $^{14}$C-aminopyrine (herein abbreviated as [$^{14}$C]AF) accumulation by parietal cells in dose dependent fashion, which is a typical test for measuring the gastric acid secretion by parietal cells (American J. Physiol., 238 G366-375, 1980), induced by many types of secretagogues without altering the receptor binding of those secretagogues and the activation of the immediate post-receptor signal transduction cascades. Therefore, the MLCK inhibitor can be an excellent treating agent for peptic ulcer. Unless otherwise indicated herein, all parts, percents, ratios and the like are by weight.

EXAMPLE

1) Chemicals

Carbachol, histamine, forskolin, dibutyryl cAMP (DBcAMP), isobutylmethylxanthine (IMX), dinitrophenol, ethylenediaminetetraacetic acid (EDTA), bovine serum albumin (BSA) and collagenase (type I) were purchased from Sigma Chemical (St. Louis, Mo.). Human gastrin I was obtained from Penisula Lab. Inc. (Belmont, Calif.). N-2-hydroxyethylpiperazine-N'-2-ethanesulfonic acid (HEPES) was obtained from Calbiochem-Behringer La Jolla, Calif.), dimethylsulfoxide (DMSO) from Fluka (Hauppauge, N.Y.), TS-1 from Research Products International (Mount Prospect, Ill.) and Ecolite from ICN Biochemicals (Irvine, Calif.). [$^{14}$C]aminopyrine (80 Ci/mmol), [$^3$H] cAMP assay kit and [$^3$H]1,4,5-triphosphate assay kit were products from Amasham (Arlinton Heights, Ill.). Hank's balanced salt solution was purchased from Irvine Scientific (Santa Ana, Calif.), and Earle's balanced salt solution (EBSS) from Gibco (Grand Island, N.Y.). ML-9 was purchased from Seikagaku America (Rockville, Md.) and Fura-2AM from Molecular Probes Inc. (Eugene, Oreg.).

2) Parietal Cell Preparation

Cells were dispersed from adult canine mucosa by sequential incubation with collagenase (0.35 mg/ml) and EDTA (1 nM), following the procedure of Soll (J. Clin. Investi. 61 370-380 1978). The dispersed cells were further enriched by counterflow elutriation with a Beckman JE-6B elutriator (Backman, Fullerton, Calif.).

The fraction of cells was >70% parietal cells with >95% viability, as assessed by trepan blue exclusion.

3) Parietal Cell Activity

Carbachol (final concentration: $10^{-4}$ M), histamine ($10^{-4}$ M), gastrin ($10^{-7}$ M) and DBcAMP ($10^{-4}$ M) were dissolved in distilled water. ML-9 (final concentration: $10^{-8}$ M to $5 \times 10^{-6}$ M) and forskolin (final contentration: $10^{-4}$ M) were dissolved in ethanol. IMX (final concentration: $10^{-4}$ M) was dissolved in 0.1 N NaOH and neutralized using 0.1 N HCl. The accumulation of [$^{14}$C]AP was used as an indicator of parietal cell acid secretory activity (Am. J. Physiol., 238 G366-375 1980). [$^{14}$C ]AP, ML-9 and various test agents were added to $5 \times 10^5$ cells suspended in 2 ml of EBSS containing 10 mM HEPES, 2 mM glutamate, 0.22% NaHCO$_3$ and 0.1% BSA. The control contained 1% ethanol. After incubation in 5%CO$_2$—95%air for 20 min at 37° C. in a shaking water bath, the cell suspension (0.5 ml) was removed, layered over ice-chilled Hanks' balanced salt solution containing 0.1% BSA and 25 mM HEPES (0.75 ml) in 1.5 ml microfuge tubes (Sartedt, Pinceton, N.J.) and centrifuged for 45 seconds in a Beckman microfuge. The cell pellets were dissolved in 0.8 ml of TS-1, Ecolite, scintillation cocktail, containing 1% acetic acid was added and samples were counted in a Beckman liquid scintillation counter. The accumulation of [$^{14}$C]AP in the presence of dinitrophenol (0.1 mM) was considered to represent nonspecific uptake and thus was subtracted from test values. ML-9 was mixed with a small volume of ethanol. The final media concentration of ethanol in these procedures (1%) had no effect on basal or secretagogue stimulated aminopyrine accumulation by parietal cells.

4) 1,4,5-IP$_3$

900 μl of parietal cells ($5 \times 10^6$ cells) in EBSS containing 10 mM HEPES, 2 mM glutsmate, 0.22% NaHCO$_3$, 0.1% BSA were incubated for 30 seconds in the presence of ML-9 ($10^{-6}$ M) and 100 μl of the test substances. 0.5% of ethanol was present in the control. Incubations were terminated by addition of 250 μl of chilled 25% perchloric acid and were neutralized with 10 N KOH and the mixture was centrifuged at 3000 rpm for 10 min at 4° C. The amount of 1,4,5-IP$_3$ was measured using a competitive protein binding assay using a kit obtained from Amasham. Carbachol ($10^{-4}$ M), histamine+IMX ($10^{-4}$ M) and gastrin ($10^{-7}$ M) were used as the test substances.

5) cAMP Production

Parietal cells ($5 \times 10^6$ cells/2 ml) were incubated for 15 min at 37° C. in EBBS containing 10 mM HEPES, 2 mM glutamare, 0.22% NaHCO$_3$, 0.1% BSA, ML-9 ($10^{-6}$ M) and the test substances under an atmosphere of 5%CO$_2$—95%air. One % ethanol was present in the control. The incubations were terminated by adding 0.5 ml of chilled 30% trichloroacetic acid and the mixture was centrifuged at 3000 rpm for 10 min at 4° C. The supernatant was extracted four times with 4 ml of diethyl ether saturated with water, the aqueous phase was lyophilized, the amount of cAMP was measured using a competitive protein binding assay using a kit obtained from Amesham. Carbachol ($10^{-4}$ M), histamine+IMX ($10^{-4}$ M) and forskolin ($10^{-4}$ M) were used as the test substances.

6) [Ca$^{2+}$]i in Single Parietal Cell

Parietal cells ($1 \times 10^{-6}$ cells/ml) were incubated with 1 μM of Fura 2-AM for 20 min at 37° C. in EBSS containing 10 mM HEPES, 2 mM glutamate, 0.22% NaHCO$_3$, 0.1% BSA. The procedures utilized a dual-wavelength modular fluorometer system (spex-CM30) coupled to a Nikon Diapot inverted microscope. Cells were placed on a glass cover clip coated with Cell Tak mounted on the bottom of a chamber (0.1 ml of vol) kept at 37° C. A single parietal cell was piked up under microscope. Cells were perfused with 10 mM HEPES buffer containing 120 mM NaCl, 2.5 mM K$_2$HPO$_4$, 0.5 mM CaSO$_4$, 0.18% glucose (pH 7.35) and fluorescence (340 nm and 380 nm) from a single parietal cell was quantified.

7) Results

Figure 2:
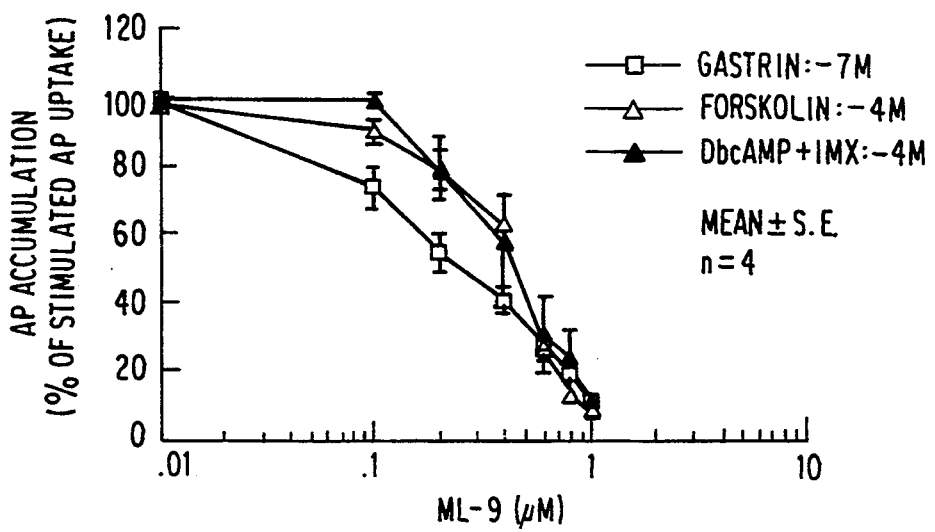
Figure 3:
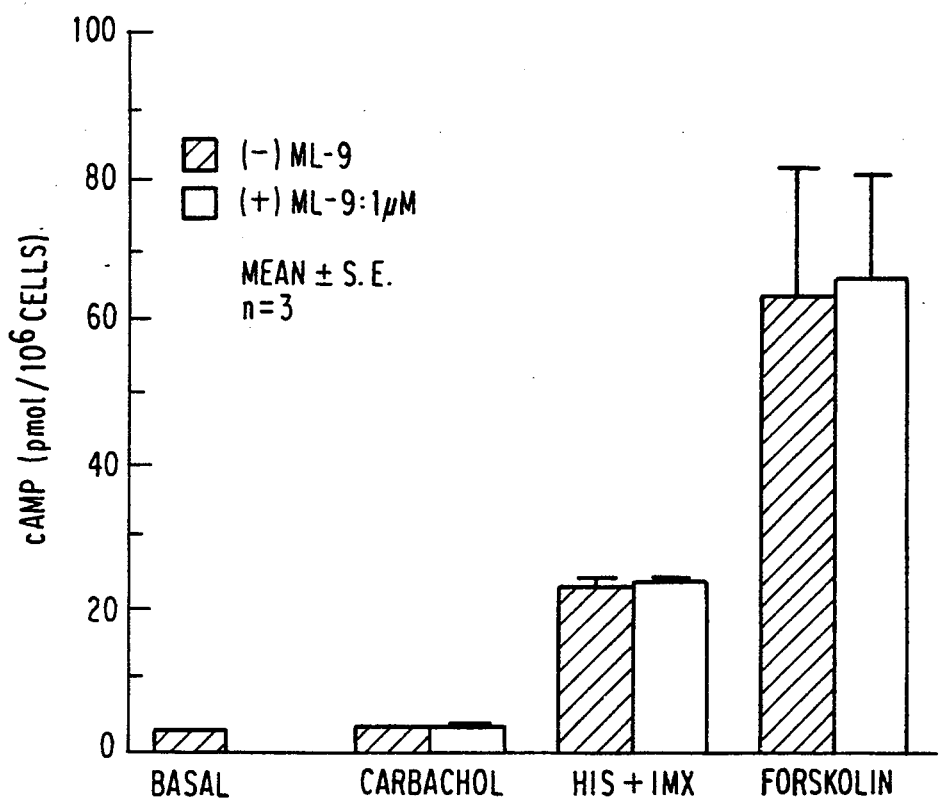
FIG. 3 demonstrates the effect of ML-9 on cAMP generation of carbachol, histamine+IMX and forskolin stimulated parietal cells.
Figure 4:
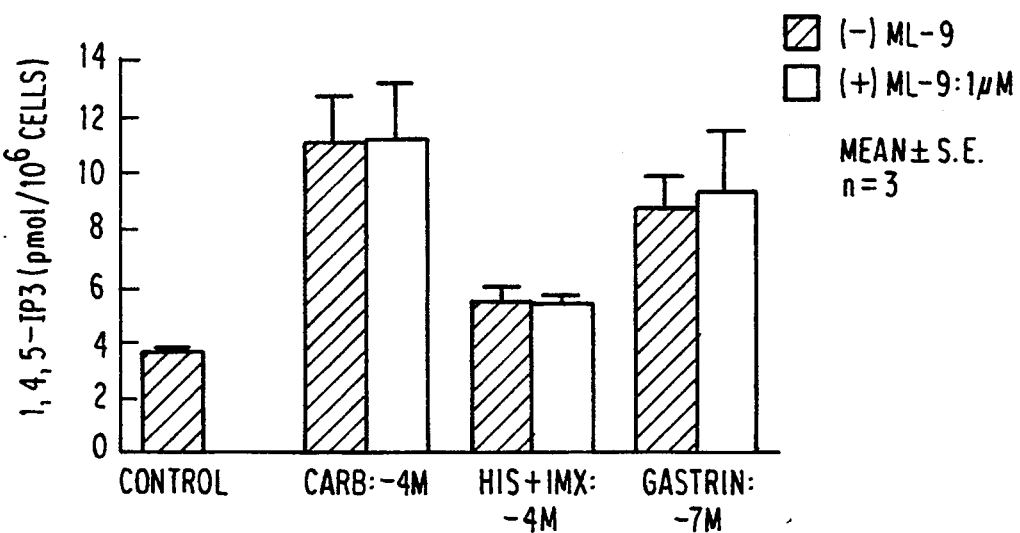
FIG. 4 demonstrates the effect of ML-9 on 1,4,5-$IP_3$ generation of carbachol, histamine+IMX and gastrin stimulated parietal cells.
Figure 5:
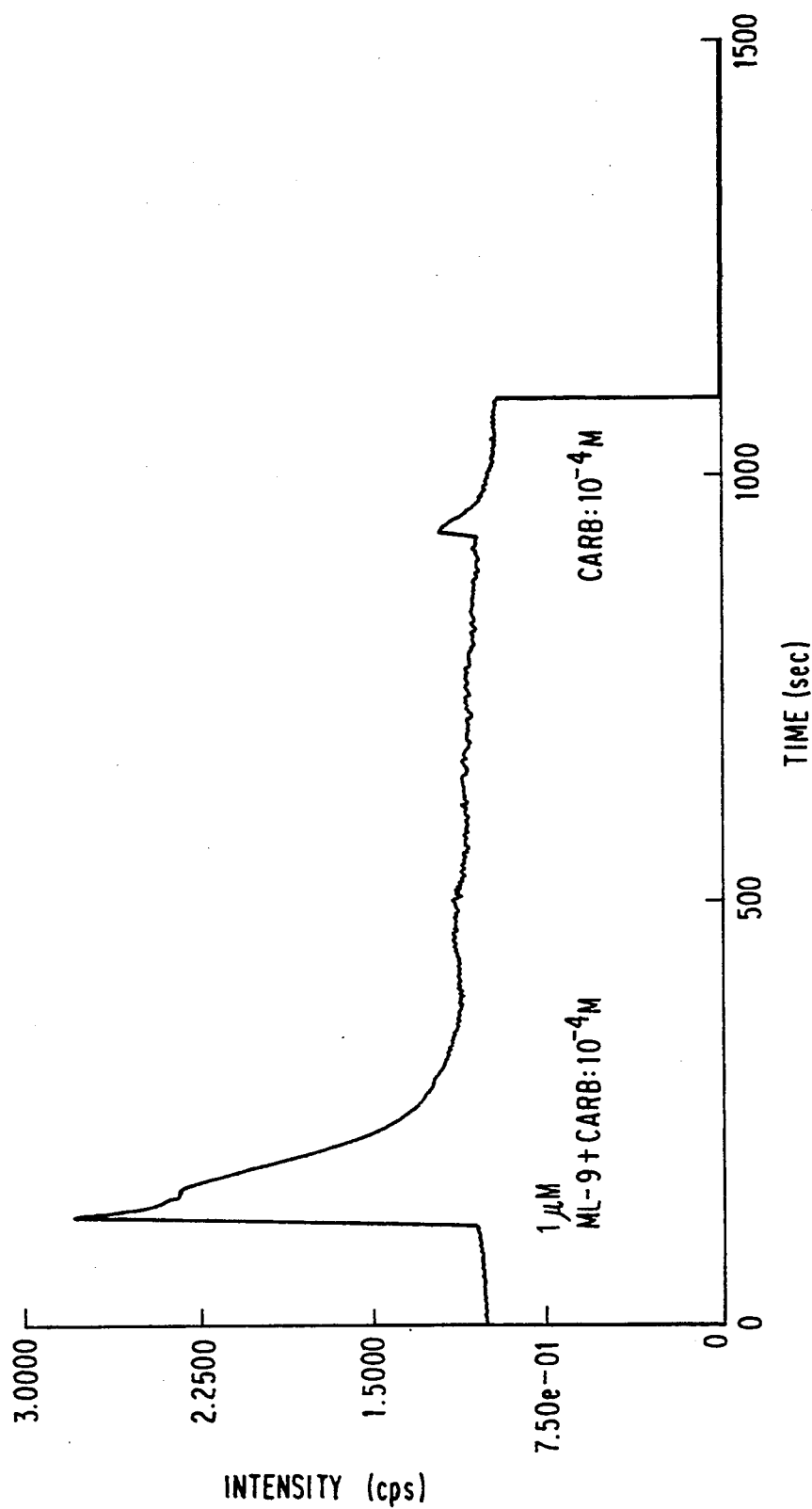
FIG. 5 demonstrates the effect of ML-9 on carbachol induced $[Ca^{2+}]i$ mobilization in a parietal cell.

MLCK selective inhibitor, ML-9 dose dependently inhibited [$^{14}$C]AP uptake of maximal stimulated parietal cells by $10^{-4}$ M carbachol, $10^{-4}$ M histamine+IMX (FIG. 1). $10^{-7}$ M gastrin, $10^{-4}$ M forskolin and $10^{-4}$ M DBcAMP+IMX (FIG. 2). Maximal inhibition was observed at $10^{-6}$ M or $5 \times 10^{-6}$ M of ML-9, about over 90% inhibition of maximal stimulated [$^{14}$C]AP uptake. As shown in Table 1 below, IC$_{50}$ of ML-9 on aminopyrine uptake stimulated by all of the secretagogues tested were similar in value at about 0.45 μM. Maximal inhibitory concentrations of ML-9 ($10^{-6}$ M) did not alter histamine and forskolin stimulated cAMP generation, carbachol and gastrin stimulated 1,4,5-IP$_3$ formation or carbachol induced [Ca$^{2+}$]i mobilization in parietal cell (FIGS. 3, 4 and 5). The data indicate the inhibition of MLCK decreases parietal cell activity induced by agents that stimulate both cAMP and Ca$^{2+}$ dependent signaling systems and MLCK inhibition exerts these effects without altering either the receptor binding or the activation of the immediate post-receptor signal transduction cascades. These findings indicate that ML-9 inhibited acid secretion in a parietal cell through the direct inhibition of MLCK and leads to the conclusions that MLCK plays a critical role at a distal point in the process of H$^+$ generation in parietal cell, and MLCK inhibitor is capable of inhibiting acid secretion and is considered useful as an anti-ulcer agent.

TABLE 1

Effect of ML-9 on $^{14}$C AP Accumulation of Secretagogue Stimulated Parietal Cell

| Secretagogue | Dose (M) | AP Uptake (% of Basal) | IC$_{50}$ of ML-9 (μM) | Maximal Inhibition (% of max.) |
|---|---|---|---|---|
| Carbachol | $1 \times 10^{-4}$ | 1189.5 ± 189.8 | 0.44 ± 0.05 | 90.8 ± 0.1 |
| Histamine + IMX | $1 \times 10^{-4}$ | 1232.5 ± 128.7 | 0.47 ± 0.06 | 89.5 ± 3.7 |
| Gastrin | $1 \times 10^{-7}$ | 179.8 ± 31.0 | 0.29 ± 0.04 | 89.3 ± 2.8 |
| Forskolin | $1 \times 10^{-4}$ | 1263.0 ± 126.8 | 0.47 ± 0.03 | 90.3 ± 3.1 |
| DbcAMP + IMX | $1 \times 10^{-4}$ | 1142.5 ± 139.4 | 0.44 ± 0.08 | 88.0 ± 1.7 | mean ± S.E.
n = 4

While the invention has been described in detail and with reference to specific embodiments thereof, it will be apparent to one skilled in the art that various changes and modifications can be made therein without departing from the spirit and scope thereof.

What is claimed is:

1. A method for treatment of peptic ulcers, which comprises administering an anti-peptic ulcer effective amount of a myosin light chain kinase inhibitor to a patient suffering from a peptic ulcer.

2. The method as claimed in claim 1, wherein the peptic ulcer is a gastric ulcer.

3. The method as claimed in claim 1, wherein the peptic ulcer is a duodenal ulcer.

4. The method as claimed in claim 1, wherein said myosin light chain kinase inhibitor is 1-(5-chloronaphthalene-1-sulfonyl)-1H-hexahydro-1,4-diazepine hydrochloride or 1-(5-iodonaphthalene-1-sulfonyl)-1H-hexahydro-1,4-diazepine hydrochloride.

5. The method as claimed in claim 1, wherein said inhibitor is in a form selected from the group consisting of a tablet, powder, capsule, granule and injectable solution.

6. The method as claimed in claim 1, wherein said myosin light chain kinase inhibitor is administered in an amount of from 1-1000 mg/day.

* * * * *